United States Patent [19]

Kamiya et al.

[11] Patent Number: 4,879,274
[45] Date of Patent: Nov. 7, 1989

[54] EXTERNAL MEDICATION FOR SKIN

[75] Inventors: Tetsuro Kamiya; Shuichi Tsuchiya; Kenji Hara, all of Utsunomiya, Japan

[73] Assignee: Kao Corporation, Tokyo, Japan

[21] Appl. No.: 906,375

[22] Filed: Sep. 12, 1986

[30] Foreign Application Priority Data

Sep. 27, 1985 [JP] Japan .................................. 60-213961

[51] Int. Cl.$^4$ ............................................. A61K 47/00
[52] U.S. Cl. ...................................... 514/12; 474/449;
514/29; 514/31; 514/39; 514/52; 514/110;
514/152; 514/154; 514/167; 514/174; 514/178;
514/179; 514/180; 514/182; 514/258; 514/270;
514/271; 514/274; 514/280; 514/282; 514/295;
514/301; 514/312; 514/356; 514/357; 514/396;
514/404; 514/420; 514/427; 514/450; 514/458;
514/472; 514/481; 514/509; 514/517; 514/536;
514/544; 514/548; 514/567; 514/569; 514/570;
514/622; 514/626; 514/627; 514/628; 514/629;
514/635; 514/648; 514/725; 514/727; 514/729;
514/763; 514/777; 514/947

[58] Field of Search ................... 424/449; 514/947, 12,
514/29, 31, 39, 52, 110, 152, 154, 167, 174, 178,
179, 180, 182, 223, 258, 270, 271, 274, 280, 282,
295, 301, 312, 356, 357, 396, 404, 420, 427, 450,
456, 472, 481, 509, 517, 536, 544, 548, 567, 569,
570, 622, 626, 627, 628, 629, 635, 648, 725, 727,
729, 763, 777

[56] References Cited

PUBLICATIONS

Shiseido, I, Chem Abs 94, 109092 (1980).
Shiseido II, Chem Abs 93, 191909 (1980).
Iwata, Chem Abs 84, 155519 (1974).
Takaishi, Chem Abs 95, 97052r (1981).
Kao, Chem Abs 101, 191133 (1984).

Primary Examiner—Mark L. Berch
Attorney, Agent, or Firm—Oblon, Spivak, McClelland, Maier & Neustadt

[57] ABSTRACT

Novel external medications comprise, as essential components, the following three components (A) to (C):

(A) an α-monoglyceryl ether represented by the following formula (I):

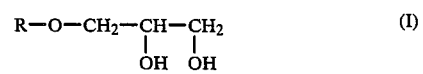

wherein R means an alkyl or alkenyl group having 10 - 24 carbon atoms;
(B) a physiologically active material; and
(C) an oily material.

The external medications have extremely high skin occlusive properties and significantly-improved absorptivity of phosiologically active materials. Therefore, a smaller amount of the medications compared with the conventional ones can give sufficient pharmacological effects and thus side effects can be reduced. The external medications may contain physiologically active materials such as drugs, growth hormones and the like, which are expected to show pharmacological effects upon their percutaneous absorption.

20 Claims, No Drawings

EXTERNAL MEDICATION FOR SKIN

BACKGROUND OF THE INVENTION

1. Field of the Invention

This invention relates to external medications, more specifically to external medications having excellent skin occlusive properties.

2. Description of the Prior Art

It has been known that outdoor winter air conditions, domestic kitchen work, miscellaneous house work and the like tend to cause crazing, chapping or the like, especially, in the skin of women and to aggravate housewives eczema, keratodermia tylodes palmaris progressiva, etc. It has also been known that atopic dermatitis and xerosis senilis aggravate in winter. Although various creams, ointments and the like have been placed on the market in order to improve and treat such xerodermia, creams or ointments having remarkable effects do not appear to have been provided yet. For various skin diseases to which non-steroidal antiinflammatory drugs or steroidal antiinflammatory drugs are applied, creams, ointments and the like containing a variety of drugs have been developed and placed on the market for many years. The effects of these external medications are however still weak and under the circumstances, their therapeutic results are very poor. As to steroid-containing external medications, the steroids which are medicinally-effective components have themselves poor percutaneous absorption and under the circumstances, they can exhibit therapeutic effects only by occlusive dressing technique (ODT).

On the other hand, two causes have generally been accepted as principal causes for xerodermia of the skin, one being loss of lipids from the skin surface and the other loss of water in the corneum. For these reasons, a preparation form capable of suppressing transpiration of water from the skin surface, that is, a preparation form having water tightness has been considered to be highly effective in easing the skin xerodermia. Preparations containing an oily component, e.g., vaseline or the like as a base have hence been used widely. In spite of their high occlusive effects against water diffusion of skin, they are accompanied by such drawbacks that they are sticky and prone to fouling and they cannot be used with comfort. Especially, preparations formed of oil in water (o/w) type creams as bases are accompanied by such shortcomings that their therapeutic effects relying upon the creamy bases are reduced because their emulsifier are hydrophilic and their water tightness are lowered and they are hence easily washed off with water.

Another therapeutic method has also been known conventionally, in which a thin plastic film is applied on a medical preparation coated on the skin in order to promote the percutaneous absorption of its medicine. However, this therapeutic method is not used too much routinely these days because the application of such a film is cumbersome.

SUMMARY OF THE INVENTION

The present inventors have carried out an extensive research with a view toward providing an external medication capable of treating skin diseases with accompanied xerodermia, being highly effective in inhibiting transpiration of water from the skin surface, that is, having high water occlusive effects, and being less sticky. As a result, it has been found that an external medication capable of satisfying the above-described requirements can be obtained by combining a specific glyceryl ether, physiologically active material and oily material, leading to completion of the present invention.

The present invention therefore provides an external medication which comprises, as essential components, the following three components (A)–(C):

(A) an α-monoglyceryl ether represented by the following formula (I):

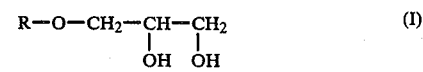

wherein R means an alkyl or alkenyl group having 10–24 carbon atoms;

(B) a physiologically active material; and (C) an oily material.

DETAILED DESCRIPTION OF THE INVENTION AND PREFERRED EMBODIMENTS

The group R in the α-monoglyceryl ether (I), which is useful as the component (A) in the present invention, is a linear or branched alkyl or alkenyl group. As exemplary linear alkyl groups, may be mentioned lauryl, myristyl, cetyl, stearyl, eicosyl and tocosyl groups. As a linear alkenyl group, oleyl group is mentioned by way of example. As branched alkyl groups, branched alkyl groups represented by the following formula (II) or (III) may be mentioned by way of example.

wherein $R_1$ and $R_2$ denote individually a linear or branched alkyl group.

As exemplary alkyl groups having side chains at their β-positions as shown above, may be mentioned 5,7,7-trimethyl-2-(1,3,3-trimethylbutyl)-octyl group, 2-heptylundecyl group, 2-hexyldecyl group and 2-octyldodecyl group.

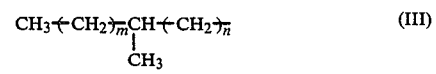

wherein m stands for an integer of 2–14, n is an integer of 3–11, and the sum of m and n is 9–21.

Such α-monoglyceryl ethers having monomethyl-branched alkyl groups may be derived, for example, after reducing monomethyl-branched alkyl-containing fatty acids, which have been obtained as byproducts upon preparation of the dimers of unsaturated fatty acids [J.A.C.S., 51, 522 (1974)], into their corresponding alcohols (Japanese Patent Laid-Open No. 113188/1981).

Among the α-monoglyceryl ethers represented by the formula (I), α-monoglyceryl ethers having branched alkyl groups, notably, monomethyl-branched alkyl groups represented by the formula (III) are suitable.

It is preferable to incorporate the component (A) in an amount of 0.1–10 wt. %, preferably, 0.1–5.0 wt. % in the external skin preparation of this invention.

No particular limitation is imposed on examples of the physiologically active material which is useful as the component (B) in the present invention, so long as drugs can be cutaneously absorbed to concentrations effective for treatment. The following materials can be mentioned as specific examples.

(1) Corticosteroids, for example, hydrocortisone, prednisolone, paramethasone, beclomethasone propionate, flumethasone, dexamethasone, dexamethasone acetate, betamethasone, betamethasone valerate, triamcinolone, triamcinolone acetonide, fluocinolone, fluocinolone acetonide, clobetasol propionate, etc.

(2) Non-steroids, for example, acetaminophen, acetylsalicylic acid, methyl salicylate, glycol salicylate, mefenamic acid, flufenamic acid, indomethacin ibuprofen, diclofenac, alclofenac, oxyphenbutazone, phenylbutazone, allantoin, l-menthol, camphor, guaiazulene, azulene, glycyrrhetic acid, dipotassium glycyrrhetiate, tinoridine hydrochloride, buhexamac, etc.

(3) Antibiotics, for example, $\beta$-lactam antibiotics (penicillins, cephalosporins and the like), oxytetracycline, fradiomycin sulfate, erythromycin, chloramphenicol, etc.

(4) Antimicrobial and fungicidal agents, for example, nitrofurazone, nystatin, clotrimazole, naphthiomate, pyrrolnitrin, amphotericin B, exalamide, chlorhexidine hydrochloride, etc.

(5) Vitamins, for example, vitamin A, ergocalciferol, cholecalciferol, vitamin $B_{12}$, tocopherol acetate, tocopherol, etc.

(6) Antihistamines, for example, diphenhydramine hydrochloride, chloropheniramine maleate, crotamiton, etc.

(7) Local anesthetics, for example, dibucaine hydrochloride, lidocaine, benzocaine, ethyl aminobenzoate, etc.

(8) Coronary vasodilators, for example, nitroglycerin, nifedipine, dipyridamole, etc.

(9) Others: antineoplastic agents such as 5-fluorourasil, cyclophosphamide, busulfan and actinomycin; narcotic analgesics such as morphine, codeine, nalorphine and pentazocine; hypnotics such as barbital and thiopental; pychotropic agents such as chloropromazine and reserpine; hormones such as estradiol and methyltestosterone; etc.

Among these drugs, dexamethasone acetate, betamethasone valerate, indomethacin, allantoin, buhexamac and clotrimazole may be mentioned as materials the percutaneous absorption of which are particularly improved by the present invention.

The amount of the component (B) to be added to the external medication of this invention may be determined suitably depending on the application purpose and dose of each material.

The component (C) useful in the practice of this invention is an oily material which is in the form of either liquid or paste at 15° C. Illustrative of the component (C) include vaseline, hydrous lanolin, liquid paraffin, natural oils and fats, esters of higher fatty acids, higher fatty acids, higher alcohols, squalane, etc.

As exemplary natural oils and fats, may be mentioned olive oil, avocado oil, camellia oil, turtle oil, mink oil, cacao butter and the like. Exemplary esters of higher fatty acids include ethyl linoleate, isopropyl myristate, decyl oleate, octyldodecyl myristate and the like. As higher fatty acids, may be mentioned, for example, lauric acid, myristic acid, palmitic acid, stearic acid, oleic acid, isostearic acid, linoleic acid and so on. As illustrative alcohols, may be mentioned dodecyl alcohol, myristyl alcohol, cetyl alcohol, stearyl alcohol, oleyl alcohol, glycerin, polyglycerin, etc.

Of these oily materials, vaseline, isopropyl myristate, octyldodecyl myristate, liquid paraffin, squalane and hydrous lanolin are particularly preferred. Two or three of these oily materials may be used as a mixture in accordance with the intended feeling and purpose of application. This can bring about still more preferable results. As one example of such combined use, isopropyl myristate, octyldodecyl myristate and squalane may be added in suitable amounts to vaseline which is the stickiest, thereby making it possible to prepare a base having less stickiness while holding occlusive properties.

This component (C) may be added in an amount of 1–90 wt. % in the external medication of this invention.

The external medication of this invention can be prepared by adding and mixing the above-mentioned three essential components in a manner known per se in the art. Although this external medication may be used, as is, as an oil-base preparation, it may also be converted into an emulsion-type external preparation for its application.

When such an emulsion-type external preparation is desired, it is unnecessary to use any additional emulsifier because the $\alpha$-monoglyceryl ether per se is an emulsifier. However, it is also possible to add, as an emulsifier or emulsion stabilizer, 0.1–20 wt. % of lecithin, the sorbitan ester of a fatty acid, the dextrin ester of a fatty acid, a fatty acid monoglyceride, a metal salt of a fatty acid, magnesium sulfate or the like. The remainder may comprise other desired components, for example, perfume, dyestuff and/or the like in addition to water.

Since the external medication is highly effective in inhibiting transpiration of water from the skin, namely, has high water-occlusive effects, it is effective in improving the percutaneous absorption of its physiologically-active material in the same manner as occlusive dressing technique.

As will hereinafter be demonstrated in the following Examples, external medications of this invention have extremely high skin occlusive properties and feature significantly-improved absorption of physiologically-active materials.

In order to achieve the same degree of pharmacological effects as conventional external medications, the external medications of this invention require drugs in smaller amounts and can hence reduce side effects. In addition, the external medications of this invention are excellent so that they can be applied to many drugs, agricultural and horticultural chemicals, growth hormone and the like, which are expected to show pharmacological effects upon their percutaneous absorption.

The present invention will hereinafter be described specifically by the following Examples. It should however be borne in mind that the present invention is not necessarily limited to the following Examples.

EXAMPLE 1

The following indomethacin-containing external medication was prepared and its percutaneous absorption was tested. Results are shown in Table 1.

Inventive Product

Formulation:
(1) $\alpha$-Mono-methyl-branched isostearyl 3.0 (g) glyceryl ether*
(2) Vaseline 25.0
(3) Isopropyl myristate 5.0

(4) Indomethacin 1.0
(5) Purified water 66.0

*In the general formula (I), R is a methyl-branched isostearyl group represented by the following formula:

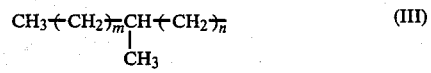 (III)

wherein m stands for an integer of 4–10, n is an integer of 5–11, and m+n is 11–17, with a proviso that m and n have distributions with peaks at m=7 and n=8 respectively.

The above components (1)–(4) were heated and mixed, and the component (5) which had been heated beforehand was then gradually added to form an emulsion.

Comparative Product 1

Formulation:
(1) α-Mono-methyl-branched isostearyl 3.0 (g) glyceryl ether
(2) Ethyl alcohol 30.0
(3) Indomethacin 1.0
(4) Purified water 66.0

The above components (1)–(3) were heated and mixed, and the component (4) which had been heated beforehand was then gradually added and mixed.

Comparative Product 2

Formulation:
(1) Vaseline 49.5 (g)
(2) Isopropyl myristate 49.5
(3) Indomethacin 1

The above components (1), (2) and (3) were heated and mixed.

Percutaneous absorption test on indomethacin

Seven Japanese white female rabbits, each having a body weight of about 3 kg were used to constitute each group. The external preparations of the present invention and the comparative products were separately coated at a dose equivalent to 20 mg of indomethacin on the shaved normal abdominal skin (10 cm×14 cm) of the rabbits in the corresponding groups. Upon elapsed time of 4, 10 and 20 hours, blood samples were respectively collected from their auricular veins to measure the blood levels of indomethacin.

Results:

TABLE 1

| Preparation | Maximum blood level ($C_{max}$; n g/ml) |
|---|---|
| Inventive Product | 550 |
| Comparative Product 1 | 235 |
| Comparative Product 2 | 20 |

It is clearly envisaged that the external indomethacin medication of this invention showed an extremely high blood level compared with the comparative products.

EXAMPLE 2

Allantoin-containing external medications were next prepared. A clinical test was conducted with respect to xerosis senilis.

Inventive Product

Formulation:
(1) α-Mono methyl-branched isostearyl 3.0 wt. % glyceryl ether
(2) Vaseline 20.0
(3) Octyldodecyl myristate 12.0
(4) Allantoin 2.0
(5) Purified water 63.0

The above components (1), (2) were heated, and the components (3), (4) which had been mixed, heated and mixed beforehand were then gradually added to form an emulsion.

Comparative Product

A commercial urea-containing ointment (o/w cream)

Clinical test

A simple application test was conducted by the paired left-to-right comparison method on 20 male and female patients who suffered from xerosis senilis.

Results 1: Measurement of skin water contents

A site suffering most severely from xerodermia throughout the body of each of the 20 patients was chosen and the inventive product and the commercial ointment, which contained 20% of urea, were simply applied side by side there, twice a day (in the morning and in the evening) for 1 week. One day after the final application, the skin water contents (skin conductance) of the thus-applied areas were then measured by means of a capacitance conductance meter (manufactured by I.B.S. Corporation). Results are shown in the following Table.

| Preparation | Skin conductance (average) |
|---|---|
| Inventive product | 85 μmho |
| Comparative product | 40 μmho |
| Untreated | 41 μmho |

From the above results, the invention product was found to have excellent sealing effects.

Results 2: Clinical results

By the double-blind test, the inventive product and commercial urea-containing ointment were simply applied twice a day (in the morning and in the evening) for 1 week to affected areas of the patients. The drugs were evaluated on the 20 patients as follows.

| | Inventive product | Commercial urea-containing ointment |
|---|---|---|
| Extremely effective | 3 | 0 |
| Effective | 10 | 0 |
| Slightly effective | 6 | 4 |
| Ineffctive | 1 | 13 |
| Harmful | 0 | 3 |

Unit: patient(s)

In the harmful cases of the commercial product, the application of the commercial product was stopped before the end of the test, primarily due to pricking or tingling feeling.

The invention product alleviated the itchy symptom of the patients and showed remarkable improvements to the xerodermia.

EXAMPLE 3

The following external medication containing the steroid hormone given below was prepared, on which a skin vasoconstriction test and inhibitory test of carrageenin caused edema were conducted.

Inventive Product

Formulation:
(1) α-Mono-methyl-branched isostearyl 2.0 (g) glyceryl ether
(2) Vaseline 40.0
(3) Betamethasone valerate 0.12
(4) Purified water 57.88

The above components (1)–(3) were heated into a melt, and the component (4) which had been heated beforehand was then gradually added to form an emulsion.

Comparative Example 1

Formulation:
(1) α-Mono-methyl-branched isostearyl 2.0 (g) glyceryl ether
(2) Betamethasone valerate 0.12
(3) Ethyl alcohol 30.0
(4) Purified water 67.88

The components (1)–(4) were heated and mixed.

Comparative Example 2

Commercial Product A (steroid-containing external ointment: vaseline base)
(Effective component)
Betamethasone valerate 0.12 wt. %

Comparative Example 3

Commercial Product B (steroid-containing external cream: o/w emulsion)
(Effective component)
Betamethasone valerate 0.12 wt. %

Skin vasoconstriction test

The invention products and the products of Comparative Examples 1–3 were separately applied, in a prescribed amount, on commercial adhesive plasters for patch tests. A skin vasoconstriction test was then conducted on the backs of 10 people by a usual method. The application time was set for 4 hours. Four hours after removal of each plaster, the paleness was ranked.

Ranking standard for paleness:

| | |
|---|---|
| 0 | No paleness was observed. |
| 1.0 | Paleness with unclear boundary. |
| 2.0 | Paleness with distinct boundary. |
| 3.0 | Clear Paleness with distinct boundary |

Results:

| Preparation | Paleness (average value) |
|---|---|
| Inventive Product | 3.0 |
| Comparative Product 1 | 1.6 |
| Comparative Product 2 | 0.1 |
| Comparative Product 3 | 0.2 |

The inventive product was found to feature good percutaneous absorption of the steroid and hence to show its effects promptly.

Inhibition test of carrageenin caused edema

Ten Wistar male rats, each, having a body weight of about 110 g were used to constitute each group. Before the test, the volumes of the right rear paws of the rats in each group were measured by using a branched glass container. To the right rear paw sole of each rat, 0 125 ml of a 1% aqueous solution of carrageenin was subcutaneously injected. Immediately after the injection, 0.3 g of the steroid-containing external medication was applied to the skin of the right rear paw sole. The rats of a control group were each injected simply with carrageenin. Thereafter, the volume of the rear paw of each rat was measured every 90 minutes until 6 hours after.

The rate of edema and the inhibition rate of edema (%) were calculated as follows:

$$\frac{\text{Rate of edema (\%)}}{100} = \frac{\text{Paw volume after injection}}{\text{Paw volume before injection}} - 1$$

$$\frac{\text{Inhibition rate of edema (\%)}}{100} = 1 - \frac{\text{Rate of edema (\%) in the treated group}}{\text{Rate of edema (\%) in the control group}}$$

Results:

| Preparation | Inhibition Rate of Edema (%) | | | |
|---|---|---|---|---|
| | 1.5 hr. | 3.0 hrs. | 4.5 hrs. | 6.0 hrs |
| Inventive Product | 32.1 | 39.3 | 38.5 | 37.7 |
| Comparative Product 1 | 19.8 | 20.5 | 23.1 | 22.1 |
| Comparative Product 2 | 5.1 | 7.1 | 5.8 | 4.9 |
| Comparative Product 3 | 4.5 | 4.8 | 5.1 | 5.4 |

As apparent form the above results, the external medication of this invention showed extremely high rate of preventing the edema caused by carrageenin owing to the pharmacological effect of the steroid, as compared to the comparative products.

EXAMPLE 4

The following clotrimazole-containing external medication was prepared and its clinical test was conducted with respect to ringworm of feet.

Inventive Product

Formulation:
(1) α-Mono-methyl-branched isostearyl 3.0 (g) glyceryl ether
(2) Squalane 15.0
(3) Vaseline 30.0
(4) Clotrimazole 1.0
(5) Purified water 51.0

The above components (1)–(4) were heated and mixed, and the component (5) which had been heated beforehand were then gradually added to form an emulsion.

Comparative Product

Formulation:
(1) α-Mono-methyl-branched isostearyl 3.0 (g) glyceryl ether
(2) Clotrimazole 1.0
(3) Ethyl alcohol 30
(4) Purified water 66

The above components (1)–(4) were heated and

Comparative Example 2

Commercial Product (clotrimazole-containing external cream: o/w emulsion)
(Effective component)
Clotrimazole 1.0 wt. %

Clinical test

Thirty patients suffering from ringworm of feet (herpetic ringworm, interdigital ringworm), the ages of which ranged from 19 to 54, were chosen. After initial diagnosis, the Inventive Product and Comparative Products 1 and 2 were simply applied twice a day, in the morning and in the evening by the double-blind test to patients having substantially the same degree of exanthema on both feet. The degree of improvement of the exanthema was observed after the initial application of the drugs and in the 2nd and 4th weeks to evaluate their effectiveness.

Results:

|  | Evaluation (unit: patients) | | | | |
| --- | --- | --- | --- | --- | --- |
| Drug used | Extremely effective | Effective | Slightly effective | Ineffective | Harmful |
| 2nd week | | | | | |
| Inventive Product | 7 | 2 | 1 | 0 | 0 |
| Comparative Product 1 | 2 | 5 | 2 | 1 | 0 |
| Comparative Product 2 | 0 | 3 | 5 | 2 | 0 |
| 4th week | | | | | |
| Inventive Product | 9 | 1 | 0 | 0 | 0 |
| Comparative Product 1 | 4 | 5 | 1 | 0 | 0 |
| Comparative Product 2 | 0 | 4 | 4 | 2 | 0 |

As apparent from the above results, the external medication of this invention showed extremely high alleviation of exanthema owing to the pharmacological effect of clotrimazole, compared with the comparative products.

What is claimed is:

1. An external medication comprising as essential components:
   (A) an α-monoglyceryl ether having formula (I):

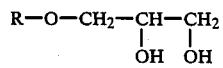
   (I)

wherein R is a $C_{10-24}$ alkyl or alkenyl group;
   (B) a physiologically active material selected from the group consisting of corticosteroids, antimicrobial agents, fungicidal agents, vitamins, antihistamines, local anesthetics and coronary vasodilators; and
   (C) an oily material which is in the form of a liquid or paste at 15° C.

2. An external medication comprises as essential components:
   (A) an α-monoglyceryl ether having the formula

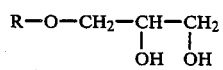
   (I)

wherein R is $C_{10-24}$ alkyl or alkenyl group;
   (B) a physiologically active material selected from the group consisting of acetaminophen, acetylsalicylic acid, methyl salicylate, glycol salicylate, mefenamic acid, flufenamic acid, indomethacin ibuporfen, diclofenac, alclofenac, oxyphenbutazoone, phenylbutazone, allantoin, l-menthol, camphor, guaiazulene, azulene, glycyrrhetic acid, dipotassium glycyrrhetiate, tinoridine hydrochloride, 5-fluorourasil, cyclophosphamide, busulfan, actinomycin, morphine, codeine, nalorphine, pentazocine, barbital, thiopental, chlorpromazine, reserpine, estradiol, and methyltestosterone; and
   (C) an oily material which is in the form of a liquid or paste at 15° C.

3. The medication of claim 1, wherein said corticosteroid is selected from the group consisting of hydrocortisone, prednisolone, paramethasone, beclomethasone propionate, flumethasone, dexamethasone, dexamethasone acetate, betamethasone, betamethasone valerate, triamcinolone, triamcinolone acetonide, fluocinolone, fluocinolone acetonide and clobetasol propionate.

4. The medication of claim 1, wherein said antimicrobial agent is selected from the group consisting of β-lactam antibiotics, oxytetracyclin, fradiomycin sulfate, erythromycin and chloramphenicol.

5. The medication of claim 1, wherein said antimicrobial and fungicidal agent is selected from the group consisting of nitrofurazone, nystatin, clotrimazole, naphthiomate, pyrrolnitrin, amphotericin B, exalamide, and chlorhexidine hydrochloride.

6. The medication of claim 1, wherein said vitamin is selected from the group consisting of vitamin A, ergocalciferol, cholecalciferol, vitamin $B_{12}$, tocopherol acetate and tocopherol.

7. The medication of claim 1, wherein said antihistamine is selected from the group consisting of diphenylhydramine hydrochloride, chloropheniramine maleate and crotamiton.

8. The medication of claim 1, wherein said local anesthetic is selected from the group consisting of dibucaine hydrochloride, lidocaine, benzocaine and ethyl aminobenzoate.

9. The medication of claim 1, wherein said coronary vasodilator is selected from the group consisting of nitroglycerin, nifedipine and dipyridamole.

10. The medication of claim 1, wherein said α-monoglyceryl ether is present in an amount of 0.1–10 wt. % of said medication.

11. The medication of claim 1, wherein said α-monoglyceryl ether is present in an amount of 0.1–5.0 wt. % of said medication.

12. The medication of claim 1, wherein component (C) is present in an amount of 1–90 wt. % of said medication.

13. The medication of claim 1, wherein said oily material is selected from the group consisting of vaseline, hydrous lanolin, liquid paraffin, natural oils and fats, esters of higher fatty acids, higher fatty acids, higher alcohols, squalane and mixtures thereof.

14. The medication of claim 13, wherein said natural oil and fats are selected from the group consisting of olive oil, avocado oil, camellia oil, turtle oil, mink oil, cacao butter.

15. The medication of claim 1, wherein said oily material is selected from the group consisting of vaseline, isopropyl myristate, octyldodecyl myristate, liquid paraffin, squalane, hydrous lanolin, and mixtures thereof.

16. The medication of claim 2, wherein component (A) is present in an amount of 0.1–10 wt. % of said medication.

17. The medication of claim 2, wherein said oily material is selected from the group consisting of vaseline, hydrous lanolin, liquid paraffin, natural oils and fats, esters of higher fatty acids, higher fatty acids, higher alcohols, squalane and mixtures thereof.

18. The medication of claim 2, wherein said oily material is selected from the group consisting of vaseline, isopropyl myristate, octydodecyl myristate, liquid paraffin, squalane, hydrous lanolin and mixtures thereof.

19. The medication of claim 2, wherein component (C) is present in an amount of 1–90 wt. % of said medication.

20. The medication of claim 16, wherein component (A) is present in an amount of 0.1–5.0 wt. % of said medication.

* * * * *